US008357659B2

(12) United States Patent
Deval et al.

(10) Patent No.: US 8,357,659 B2
(45) Date of Patent: Jan. 22, 2013

(54) METHOD OF TREATING PAIN OR ITCHING WITH APETX2 PEPTIDE TOXIN

(75) Inventors: Emmanuel Deval, Golfe Juan (FR); Sylvie Diochot, Valbonne (FR); Michel Lazdunski, Nice (FR); Eric Lingueglia, Nice (FR); Jacques Noel, Nice (FR)

(73) Assignees: Centre National de la Recherche Scientifique-CNRS, Paris (FR); Universite Nice Sophia Antipolis, Nice (FR)

( * ) Notice: Subject to any disclaimer, the term of this patent is extended or adjusted under 35 U.S.C. 154(b) by 0 days.

(21) Appl. No.: 12/995,954

(22) PCT Filed: Jun. 4, 2009

(86) PCT No.: PCT/FR2009/000657
§ 371 (c)(1),
(2), (4) Date: Feb. 28, 2011

(87) PCT Pub. No.: WO2009/147326
PCT Pub. Date: Dec. 10, 2009

(65) Prior Publication Data
US 2011/0152197 A1 Jun. 23, 2011

(30) Foreign Application Priority Data
Jun. 6, 2008 (FR) ..................... 08 03158

(51) Int. Cl.
*A61K 38/16* (2006.01)
*C07K 14/00* (2006.01)
(52) U.S. Cl. .................. 514/18.3; 514/17.4; 514/21.3; 530/300; 530/324
(58) Field of Classification Search .......... None
See application file for complete search history.

(56) References Cited

U.S. PATENT DOCUMENTS
2008/0181881 A1 7/2008 Chen et al.

OTHER PUBLICATIONS

Wells, J.A. (1990). Additivity of mutational effects in proteins. Biochemistry. 29(37):8509-8517.*

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Emmanuel Deval et al., "ASIC3, a sensor of acidic and primary inflammatory pain", The EMBO Journal, 2008, 3047-3055, vol. 27(22).
Chih-Cheng Chen, "ASIC3 and Muscle Pain", Institute of Biomedical Sciences, 2008, 225-232.
Sylvie Diochot et al., "A new sea anemone peptide, APETx2, inhibits ASIC3, a major acid-sensitive channel in sensory neurons", The EMBO Journal, 2004, 1516-1525, vol. 23 (7).
Chih-Cheng Chen et al., "A role for ASIC3 in the modulation of high-intensity pain stimuli", PNAS, Jun. 25, 2002, 8992-8997, vol. 99, (13).
Tomohiro Honma et al., Peptide Toxins in Sea Anemones: Structural and Functional Aspects, Marine Biotechnology, 2005,1-10, vol. 8, (1).
Derek C. Molliver et al., "ASIC3, an acid-sensing ion channel, is expressed in metaboreceptive sensory neurons", Molecular Pain, Nov. 23, 2005, 35, vol. 1, (1).
Nicolas Voilley et al., "Nonsteroid Anti-Inflammatory Drugs Inhibit Both the Activity and the Inflammation-Induced Expression of Acid-Sensing Ion Channels in Nociceptors", The Journal of Neuroscience, Oct. 15, 2001, 8026-8033, vol. 21 (20).
Sylvie Diochot et al., "Peptides inhibitors of acid-sensing ion channels", Toxicon, 2007, 271-284, vol. 49 (2).
Benjamin Chagot et al., "Solution structure of APETx2, a specific peptide inhibitor of ASIC3 proton-gated channels", Jun. 29, 2005, 2003-2010, vol. 14 (8).

* cited by examiner

*Primary Examiner* — Christine J Saoud
*Assistant Examiner* — Jon M Lockard
(74) *Attorney, Agent, or Firm* — Arent Fox LLP

(57) ABSTRACT

The invention relates to the use of the peptide toxin APETx2 that blocks the ASIC3 cationic channels and that is derived from the *Anthopleura elegantissima* sea anemone, and to the use of the analogs and derivatives thereof as a drug, particularly as an analgesic pain associated with the activation of ASIC3 (Acid Sensing Ion Channel 3) channels, in particular pain occurring upon an inflammation and potentially upon any painful situation associated with tissue acidosis (ischemiae, fractures, hematoma, oedema, phlyctena, local infections, tissue lesions, ocular wounds, tumours, etc.).

10 Claims, 7 Drawing Sheets

METHOD OF TREATING PAIN OR ITCHING WITH APETX2 PEPTIDE TOXIN

CROSS-REFERENCE TO RELATED APPLICATION

This application is a National Stage entry of International Application No. PCT/FR2009/000657, filed Jun. 4, 2009, which claims priority to French Patent Application No. 08/03158 filed Jun. 6, 2008, the disclosure of the prior application is incorporated in its entirety by reference.

SEQUENCE LISTING

The instant application contains a Sequence Listing which has been submitted in ASCII format via EFS-Web and is hereby incorporated by reference in its entirety. Said ASCII copy, created on Jun. 14, 2012, is named 21305336.txt and is 1,423 bytes in size.

TECHNICAL FIELD OF THE INVENTION

The invention relates to the use of the APETx2 peptide toxin that blocks the ASIC3 cationic channels and which is derived from the *Anthopleura elegantissima* sea anemone for its analgesic effects on pain associated with activation of the isoform ASIC3 (Acid Sensing Ion Channel 3) during inflammation and also potentially during any painful conditions associated with tissue acidosis (ischaemia, fractures, haematomas, oedema, blisters, local infections, tissue lesions, eye injuries and tumours, etc. . . . ).

FORMER STATE OF THE ART

Consideration and treatment of pain, particularly inflammatory pain, are fundamental aspects of improvement of patients' quality of life and are essentially based on prescription of anti-inflammatory drugs, whether non-steroidal anti-inflammatory drugs (NSAID's) or steroidal anti-inflammatory drugs. When NSAID's and/or corticosteroids are inadequate in relieving inflammatory pain, the prescriber combines a non anti-inflammatory analgesic agent, such as paracetamol, with weak or strong opioids. However, in spite of the diversity of the existing therapeutic arsenal, many types of pain show little response to the known drugs which may furthermore give rise to undesirable side effects, as is the case with NSAID's. The discovery of new analgesic targets would therefore represent a genuine advancement in this context. Ion channels occupy a particularly significant position among the molecular targets identified during the past few years, since they are directly involved in detection and transmission of pain signals by nociceptive fibres.

ASIC's (Acid Sensing Ion Channels) are cationic channels activated by extracellular acidosis (for review, [ref. 1] and [ref. 2]). To date, four genes coding for at least seven subunits (ASIC1a, ASIC1b, ASIC1b2, ASIC2a, ASIC2b, ASIC3 and ASIC4) have been identified in mammals. Functional ASIC channels result from the association of different ASIC sub-units in trimers ([ref. 3]), resulting in homomeric or heteromeric channels ([refs. 4, 5 and 6]). ASIC channels are for the most part neuronal channels, expressed both in the central and peripheral nervous systems. Whereas ASIC1a and ASIC2 channels are widely represented both in the central and peripheral nervous systems, expression of ASIC1b and ASIC3 channels is limited to sensory neurons ([refs. 7, 57 and 8]).

It has been postulated that ASIC's are capable of detecting the extracellular acidifications liable to occur during ischemia, inflammation, haematoma, fracture, lesion, a surgical operation (postoperative pain) or development of some tumours ([ref. 9]). It has indeed been known for several years now that extracellular acidosis generates pain ([refs. 11 and 12)] and experiments performed in healthy human volunteers ([refs. 13 and 14]) have demonstrated the involvement of ASIC's in acidic cutaneous pain using amiloride as well as of some NSAID's, which are non-specific inhibitors of ASIC's ([refs. 15 and 17]).

Among all the ASIC sub-units expressed in sensory neurons, ASIC3 is of specific interest given that it is widely expressed in nociceptive neurons ([ref. 7], quoted above; [refs. 17 and 18]), and that it generates a persisting, non-inactivating current in response to moderate acidification (at approx. pH 7.0) ([ref. 19]). The ASIC3 current has in fact two components: (1) a transient component which is highly pH-sensitive ($pH_{0.5}$=6.5-6.7) ([ref. 7], quoted above; [ref. 20]) rapidly activating ($t_{0.5}$<5 msec.) and inactivating ($t_{0.5}$=0.32 sec.) ([ref. 20], quoted above) and (2) a sustained component which originates in the case of moderate acidifications (between pH 7.3 and 6.7) from the window current derived from the partial overlapping of the activation and inactivation curves of the channel ([ref. 19], quoted above) and in the case of more acidic pH values (pH<6.0) from an apparently different mechanism. The transient current recovers rapidly following inactivation after return to a neutral pH ($t_{0.5}$=0.58 secs.) ([ref. 20], quoted above). By way of comparison, ASIC1a requires a much longer recovery time ($t_{0.5}$=13 secs.) ([ref. 20], quoted above). The transient current is rapidly inactivated when the resting pH is acidic. Conversely, the sustained current may still be activated when the pH decreases from a relatively acidic resting pH (<pH 6) and is likewise activated when the extracellular pH decreases gradually ([ref. 7], quoted above). Recent studies in knock-out mice suggest a role of ASIC3 in detection of tissue acidosis in muscles and joints in models of secondary mechanical hyperalgia induced by inflammation or by repeated injections of acid into the muscle ([refs. 21, 22, 23 or 60]). An involvement of ASIC3 in the mechanosensitivity of large diameter sensory neurons was also postulated ([ref. 21]). On the other hand, comparison of normal and knock-out mice was unable to reveal a significant role of ASIC3 in acidic cutaneous pain or in cutaneous sensitivity to pain associated with inflammation ([ref. 21], quoted above and [ref. 25]).

Consequently, although the past studies at best allow one to predict that inhibition of the activity of ASIC3 might at first sight affect pain, the actual involvement of ASIC's and the relative participation of the various isoforms present in the sensory neurons, particularly ASIC3, in the in vivo sensitivity of the nociceptors to acid and in acidic cutaneous pain under normal or inflammatory conditions still remain to be shown. Furthermore, it also remains to be demonstrated in what way, hyperalgesia or analgesia, inhibition of the activity of the ASIC's, particularly ASIC3, might affect pain. However, the additional analyses required call for selective pharmacological tools.

Until recently, the repertoire of active ligands capable of inhibiting ASIC3 was mainly restricted to amiloride and non-steroidal anti-inflammatory drugs (NSAID's) [ref. 7], quoted above and [ref. 17], quoted above). None of these drugs however are absolutely specific to the ASIC channels or to a particular type of ASIC channel and specifically ASIC3.

For several years, animal venoms have yielded a large number of toxins capable of specifically modifying with a high affinity the voltage-dependent $Ca^{2+}$, $K^+$ and $Na^+$ currents ([refs. 28, 29, 30, 31, 32, 33)], the $Ca^{2+}$-dependent potassium channels ([refs. 34 and 35)] and the mechanosensitive potassium channels ([ref. 58]). Two animal toxins (PcTx1 and APETx2) capable of specifically blocking the ASIC1a ([ref. 36]) and ASIC3 ([ref. 38]) channels, respectively, have recently been identified.

A very large number of scorpion, bee, spider, snake and sea anemone venoms (1/1000 dilution) or peptide fractions (0.1 mg/ml) have been screened with regard to ASIC3 channels expressed in *Xenopus oocytes* with the aim of identifying specific effectors of the ASIC3 channel. It has been demonstrated that a peptide fraction of the *Anthopleura elegantissima* sea anemone inhibits more than 80% of the current of rat ASCI3 stimulated at pH6. The active peptide was purified to homogeneity by reversed-phase and cation-exchange chromatography guided by monitoring of the fractions active on ASIC3 and was designated APETx2 ([ref. 38]).

APETx2 is a peptide of 42 amino acids (GTACSCGNSKGIYWFYRPSCPTDRGYTGSCRYFLGTCCTPAD (SEQ ID NO: 3)) comprising three disulphide bonds, with a structural organisation similar to that of other sea anemone toxins that block the voltage-sensitive potassium and sodium channels. Its complete sequence was established using Edman's N-terminal degradation and its monoisotopic mass measured (4557.96 Da) perfectly matches the mass calculated based on the sequence data (4557.88 Da, precision at 17.5 ppm), indicating a free C-terminus. APETx2 displays 64% sequence identity (76% homology) with APETx1 ([ref. 40]) and only 34% sequence identity (57 and 55% homology respectively) with the toxins BDS-I and BDS-II of Anemonia sulcata, which inhibit the voltage-gated potassium current Kv3.4 ([ref. 41]). The sequence identity with the peptides activating the sodium currents, such as AP-A, AP-B, AP-C, APE1-1 and APE-2 from Anthopleura sp. ([ref. 39]) is only 25-29% (41-47% homology). Furthermore, APETx2 does not display any sequence homology with PcTx1, the specific inhibitor of the isoform ASIC1a ([ref. 36], quoted above).

APETx2 directly blocks ASIC3 by acting on its external portion and does not modify the unit conductance of the channel. APETx2 reversibly blocks ASIC3 by inhibiting the transient current ($IC_{50}=63$ nM) without affecting the sustained current, yet does not have any effect on the ASIC1a, ASIC1b and ASIC2a isoforms. APETx2 also inhibits the current of the heteromer ASIC2b+3, whereas it has less affinity for the heteromer ASIC1b+3 and ASIC1a+3 and does not have any effect on the heteromer ASIC2a+3 ([ref. 38]), quoted above).

Surprisingly, the inventors have now shown that the peripheral injection, particularly subcutaneously, of the APETx2 peptide toxin allows a reduction in the pain (an analgesic effect) associated with activation of the isoform ASIC3 in rat models of pain related to inflammation and subcutaneous injection of acid solutions mimicking all painful situations associated with tissue acidosis (ischaemia, fractures, tissue lesions and tumours etc. . . . ).

DISCLOSURE OF THE INVENTION

The invention aims to remedy the disadvantages of the state of the art and particularly provide new analgesic molecules specific to the target that possess few or no undesirable side effects and are easy to use, in particular by peripheral administration (subcutaneous, intramuscular, transcutaneous, cutaneous, etc. . . . ).

A first aspect of the invention relates to use of the APETx2 peptide toxin of the sea anemone *Anthopleura elegantissima* and of analogues and derivatives thereof in order to obtain a drug.

The term "analogues of the APETx2 peptide toxin" means peptides isolated from other sea anemone venoms or from other marine species of the same family presenting the same property of inhibiting ASIC3-like channels. For example, the term includes peptides having 60 to 99% sequence identity with the sequence of 42 amino acids of the APETx2 peptide toxin.

The term "derivatives of the APETx2 peptide toxin" means peptides isolated from the same venom in which one or several amino acids in the sequence of 42 amino acids of the APETx2 peptide toxin have been deleted and/or added and/or suppressed and which retain the property of inhibiting ASIC3-like channels. For example, the term includes peptide variants that display substitution at the 3, 5, 8, 9, 10, 15, 16, 17, 23, 31, 32, 33, 36, 39 and/or 41 positions in the sequence of 42 amino acids of the APETx2 peptide toxin. Peptide variants displaying an extension of one or several amino acids at the N-terminal and or C-terminal ends of the sequence of the APETx2 peptide toxin may also be included.

According to a specific embodiment of the invention, said drug is intended to prevent or treat disorders involving ASIC3-like channels. For example, said pathological conditions are chosen in the group composed of inflammations including gastritis, ischaemia (muscular, cardiac, mesenteric . . . ), fractures, haematomas, oedemas, phlyctenae (or blisters or bullae), local infections, tissue lesions including incisions related to a surgical procedure, eye injuries, pruritus and tumours, including bone tumours and metastases.

In particular, said drug is an analgesic agent, preferably intended for the prevention or treatment of pain induced by the activation of the ASIC3-like channels and more preferably intended for the prevention or treatment of pain resulting from inflammation.

According to another specific embodiment of the invention, said analgesic drug is intended for prevention or treatment of the acid pain associated with the activation of ASIC3-like channels. For example, the painful situations associated with tissue acidosis are chosen from among the group composed of ischaemias (muscular, cardiac, mesenteric, . . . ) fractures, haematomas, oedemas, phlyctenae (or blisters or bullae), local infections, tissue lesions including incisions related to a surgical procedure (postoperative pain), eye injuries and within tumours (including bone tumours and metastases).

According to yet another embodiment of the invention, said analgesic agent is intended for the prevention and treatment of itching, insofar as the latter is caused by a pathological process involving similar sensory pathways ([ref. 61]) to those of the pain associated with activation of the ASIC3-like channels.

According to a specific embodiment of the invention, said drug is administered via the peripheral route, for example by the subcutaneous, intramuscular, transdermal or cutaneous route. Said drug is preferably administered via the subcutaneous route.

BRIEF DESCRIPTION OF THE FIGURES

Other characteristics and advantages of the invention will be apparent from reading the following description, with reference to the appended figures.

EXAMPLES

Example 1

Material and Method

Figure 1:
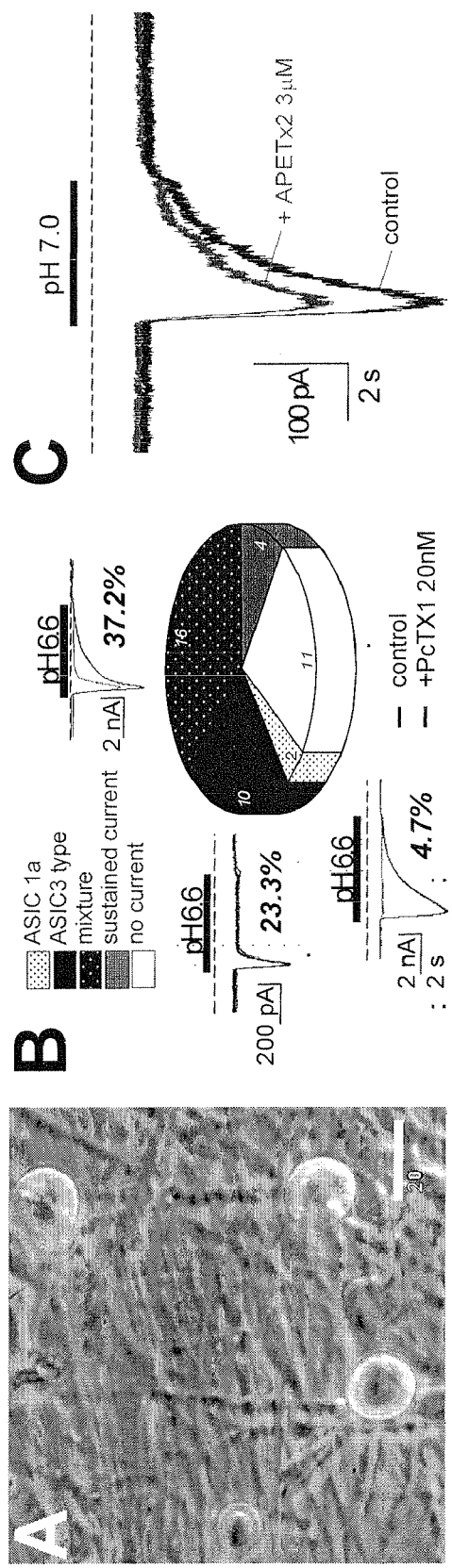
FIG. 1 is a fluorescence image of a cutaneous neuron of the spinal ganglia with retrograde labelling and of the ASIC currents recorded in these neurons.

Purification of the APETx2 Peptide Toxin of the Sea Anemone *Anthopleura elegantissima*

A polypeptide pool was isolated from a raw hydroalcoholic extract (water-methanol) of the sea anemone *Anthopleura elegantissima* ([ref. 39]), quoted above) by cation exchange chromatography on QAE Sephadex A-25 (4.5×400 nm) eluted with ammonium acetate (pH 8.3), followed by exclusion diffusion chromatography on Sephadex G50 (12×140 cm) in 1M acetic acid.

Six fractions were tested on ASIC3 channels expressed in *Xenopus oocytes* ([ref. 41], quoted above). One fraction, having inhibited more than 80% of the ASIC3 current, was purified by reversed-phase high performance liquid chromatography (HPLC) (Waters Symmetry C18, 4.6×250 mm), with a linear gradient of 10 to 40% of solvent B (acetonitrile/0.1% TFA) for 30 min. at 1 ml/min. Separation was performed on a HP1100 system (Hewlett Packard, USA) coupled to a diode array detector with UV absorbance reading at 220 and 280 nm.

The active peptide fraction was subsequently purified on a cation exchange column TSK-SP5PW (7.5×75 mm) (Tosoh, Japan) equilibrated with a mixture of water/1% acetic acid using a linear gradient of 0 to 100% of 1M ammonium acetate for 50 min., at 1 ml/min. Final purification of APETx2 was performed on the same reversed-phase HPLC column, using a linear gradient of 20 to 30%, for 10 min., followed by 30-40% of solvent B, for 20 min.

The APETx2 peptide toxin was sequenced by automated Edman's N-terminal sequencing (477A, Applied Biosystems, USA) following its reduction with 2-mercaptoethanol and its alkylation with 4-vinylpyridine. The C-terminal sequence of the peptide was confirmed by citraconylation of the arginine residues, followed by trypsin digestion. The tryptic fragments were separated by HPLC (Waters C18, 2×150 mm), using a linear gradient of 5 to 50% of acetonitrile/0.1% TFA in a mixture of water/0.1% TFA at 200 µl/min. for 40 min. The sequence homologies were determined using the BLAST program. Determination of the molecular mass was performed by MALDI-TOF mass spectrometry on a Voyager DE-PRO system (Applied Biosystems, USA) in reflector mode, with an α-cyano-4-hydroxycinnamic acid matrix (Sigma-Aldrich, USA) and internal standard. The mass spectrum was analysed using Data Explorer software and the theoretical molecular masses were calculated based on the sequence data using GPMAW software.

The arrangement of the disulphide bond of the APETx2 peptide toxin was determined using the process of partial reduction and cleavage induced by cyanylation ([refs. 42 and 56]).

A molecular model of the APETx2 peptide toxin was calculated based on the APETx1 coordinates described above ([ref. 40], quoted above), using Deep-View Swiss-PDB viewer v3.7 software. This model was optimised via the Swiss-Model server. The BDS-I coordinates (1BDS) were obtained from the PDB database. Finally, the spatial structure of the APETx2 peptide toxin was determined by nuclear magnetic resonance and essentially consists of a compact disulphide-link composed of a four-stranded β sheet ([ref. 43]).

Culture of F-11 Cell Line and Transfection

F-11 cells (refs. 44, 45, 46, 47]) were cultured in 5% of $CO_2$ at a density of 50,000 cells per 35 mm Petri dish. The culture medium contained HAM F-12 medium (Invitrogen) supplemented with 15% foetal bovine serum (ICN Biomedicals), 1×HAT (sodium hypoxanthine, aminopterine and thymidine), 200 µg/ml of allo-4-hydroxy-L-proline (Sigma-Aldrich) and 1% antibiotics. One day after seeding, the cells were transfected with ASIC1a or ASIC3 DNAc (rat clones) using Lipofectamine™ (Invitrogen) according to the manufacturer's instructions using the vectors pCI-ASIC1ar+pIRES$_2$-EGFP (ratio 1:2) or pCI-ASIC3r+pIRES$_2$-EGFP (ratio 1:10) ([ref. 36]), quoted above). For the experiments concerning the human ASIC3 clone (refer to experiments on the effects of the APETx2 toxin on the human form of the ASIC3 channel), the cells were transfected with the DNAc of human ASIC3 using the transfection agent JetPEI (Polypus Transfection) according to the manufacturer's instructions with the aid of the vector pASIC3h-IRES-EGFP. The cells were used for the patch clamp experiments (an electrophysiological method for recording ionic currents travelling through cell membranes) 2 to 4 days after transfection.

Retrograde Labelling of Cutaneous Afferences

The neurons of the dorsal root ganglion (spinal ganglia or DRG) innervating the skin were labelled by subcutaneous injections of 5×1 µl of Dil fluorescent dye (5% DMSO, Molecular Probes) in the dorsal side of the rats' hind paws. The dye was injected two weeks before the rats were sacrificed in order to prepare a primary culture of dorsal root ganglion.

Primary Culture of Neurons from Labelled Dorsal Root Ganglia

The lumbar dorsal root ganglia L3-L6 of Wistar rats (8-11 weeks) were dissected bilaterally and separated enzymatically with 0.1% collagenase. The cells were subsequently plated on 35 mm Petri dishes covered with collagen and cultured at 37° C. (95% air/5% $CO_2$) in DMEM medium containing 5% of foetal calf serum. The electrophysiological experiments were performed 1 to 8 days after seeding.

Electrophysiology

The whole cell configuration of the patch clamp method was used ([ref. 48]) in order to measure the membrane currents (imposed voltage) or the membrane potentials (imposed current). The recordings were performed at ambient temperature using an RK-400 amplifier (Bio-Logic Science Instruments) with a 3 kHz low-pass filter (Krohn-Hite). The data were sampled at 10 kHz, digitised using a Digidata 1322A A-D/D-A converter (Axon Instruments) and recorded on a hard disk using pClamp software (version 9.2.0.11, Axon Instruments). The recording probes (1-4 MOhms) contained (in mM): 135 KCl, 2.5 $Na_2$-ATP, 2 $MgCl_2$, 2.1 $CaCl_2$, 5 EGTA, 10 HEPES (pH 7.25 with KOH). Various different buffers and drugs of interest were added to the transfected cells considered individually using an internally developed microinfusion system controlled by microelectrovalves (Sirai, Italy) allowing rapid changes of solution. The control bath solution contained (in mM): 145 NaCl, 5 KCl, 2 $MgCl_2$, 2 $CaCl_2$, 10 HEPES (pH 7.4 with NaOH). The MES medium was used instead of the HEPES medium in order to buffer the solution at a pH ranging from 6 to 5, and the ASIC currents were induced by rapid changes of a control solution at pH 7.4 to an acid test solution using the microinfusion system. For the experiments conducted on the DRG neurons, glucose (10 mM) was added to the control bath solution. Hypertonic conditions were obtained by adding mannitol or sucrose to the external bath solutions, as indicated in the text.

Nociceptive Behaviour in Rats

Adult (7-8 weeks' old) male Wistar rats (Charles River, France) were placed in plastic cages with a nyctohemeral period of 12 h (with light between 8 a.m. and 8 p.m.) and with free access to food and water. The rats were left to acclimatize for at least one week before the experiments. For the behavioural experiments, the rats were placed in a transparent observation chamber where they were acclimatized for 20-30 minutes. They were subsequently immobilised while 20 µl of saline solution (0.9% or 2% of NaCl+20 mM of HEPES, $7.4 \leq pH \leq 6.6$ added or not with 10 µM of arachidonic acid and/or 10 µM of APETx2 toxin or 60 nM of PcTx1 toxin), was administered subcutaneously to the dorsal side of the right hind paw using a 30G needle connected to a 100 µl Hamilton syringe. The nociceptive behaviour (i.e. the number of hind leg quiverings) was recorded over a 5-minute period, starting immediately after the injection ([ref. 59]).

Inflammation-Induced Thermal Hyperalgesia in Rats

Sensitivity to heat of adult male Wistar rats (Charles River, France) was tested by measuring the time taken by the animal to retract one of its hind paws when placed on a hotplate at 50° C. (Bioseb, France), before and after induction of inflammation by subcutaneous injection of a solution of Freund's complete adjuvant (CFA, Sigma-Aldrich, France). The rats were acclimatised to the experimentation room for at least 30 minutes and each measurement was performed in duplicate. An initial measurement was performed before induction of inflammation. The rats were subsequently anaesthetised (isofluorane) while 150 µl of CFA diluted 1:1 with a saline solution (0.9% NaCl) containing either toxins (PcTx1 or APETx2, 120 nM and 20 µM, respectively) or the vehicle was injected (26G needle mounted on a 1 ml syringe) subcutaneously into the plantar side of one of the hind paws. The time taken by the animal to lift the injected hind paw was subsequently measured at 50° C., 2, 4 and 24 hours after the injection of CFA.

Intrathecal Injections of Interfering RNA in Rats

ASIC3 channel-specific iRNA (no. 1121; CTACACGC-TATGCCAAGGA, SEQ ID NO: 1) and its control (no. 1121S; GCTCACACTACGCAGAGAT, SEQ ID NO: 2) were designed in the laboratory and were synthesised by MWG Biotech Company (Germany). The ASIC3-specific iRNA was validated by quantification of the messenger RNA levels by quantitative RT-PCR for each ASIC channel and for the TRPV1 channel, following intrathecal injections into the lumbar region of the spinal cord of rats, at a rate of one injection per day for 3 consecutive days, before the animal was sacrificed. The same procedure was followed before induction of inflammation by CFA. Each injection was 10 µl in volume, containing 2 µg of iRNA mixed with the transfection agent i-Fect (Neuromics) at a ratio of 1 to 4.

Chemical Products

The HEPES (4-(2-hydroxyethyl)1-piperazineethanesulphonic acid) and MES media (2-(N-morpholino)ethanesulphonic acid; $C_6H_{13}NO_4S.H_2O$), mannitol, capsazepine and arachidonic acid were purchased from Sigma.

Analysis of the Data

The data were analysed using Microcal™ Origin 6.0® and GraphPad Prism 4.03 software. The data were represented as mean±standard error and the statistical difference between sets of data were assessed by using either Student's t test or one-way analysis of variance (one-way ANOVA) followed by post hoc tests when necessary.

Example 2

ASIC3 Type Current in the Neurons of the Spinal Ganglia Innervating the Skin

The ASIC currents activated by moderate extracellular acidifications were recorded in the neurons of the spinal ganglia innervating the skin in rats and were identified by retrograde labelling using the DiI fluorescent dye (FIG. 1).

The moderate pH values used in these experiments (i.e. pH 6.6 and pH 7.0) were chosen in order to mainly activate the ASIC1 and ASIC3 type currents, owing to the fact that the ASIC2 and TRPV1 type currents had been described as being activated by more drastic acidification ([ref. 49] and [ref. 2], quoted above).

FIG. 1A shows a typical DiI-positive cutaneous neuron of the spinal ganglia (arrow) used for the patch clamp experiments in whole cell configuration. These neurons have a resting membrane potential of −55.0±1.8 mV and a membrane capacitance of 39.6±1.8 pF (n=42 and 43 neurons, respectively, with data from four different cultures).

FIG. 1B shows that 65.8±6.3% of the cutaneous neurons of the spinal ganglia tested (4/7, 8/11, 8/10 and 8/15, data from four different cultures) display a transient ASIC type current induced by pH 6.6 with a mean amplitude of −60.3±16.0 pA/pF (n=28). Among the cutaneous neurons of the spinal ganglia remaining (34.2±6.3%), external application of a pH of 6.6 either does not induce any current (n=11) or induces only a small sustained current (−1.2±0.5 pA/pF, n=4).

In order to distinguish between the ASIC type currents induced by pH 6.6 in the cutaneous neurons of the spinal ganglia, the PcTx1 toxin specific to ASIC1a was used ([ref. 36], quoted above), as it is a selective inhibitor of the homomer channels ASIC1a.

FIG. 1B (right panel) shows that 4.7% (2/43) of these neurons display a current inhibited to a great extent by the toxin (>90% inhibition; i.e., ASIC1a homomer current), 23.3% (10/43) display currents insensitive to the toxin (inhibition<10%; i.e. ASIC3 type currents) and 37.2% (16/43) display partially inhibited currents ($10\% \leq inhibition \leq 90\%$; i.e., a mixture of ASIC3-type and ASIC1a homomer currents). FIG. 1C confirms participation of ASIC3 in these currents owing to their partial sensitivity to the APETx2 peptide toxin, which specifically blocks the channels containing the isoform ASIC3 ([ref. 38], quoted above).

Furthermore, use of moderate acidification (pH 6.6) in order to induce the ASIC currents in the cutaneous neurons of the spinal ganglia made it possible to exclude the majority if not all the ASIC2a-type and TRPV1 currents. The most abundant ASIC current activated by moderate acidifications in the cutaneous neurons of the spinal ganglia was therefore ASIC3-type current with a score of 60.5% (26/43).

Example 3

Potentiation by Two Inflammatory Stimuli, Osmotic Pressure and Arachidonic Acid, of Asic Current of Cutaneous Neurons of the Spinal Ganglia Activated by Moderate Acidification In damaged or inflamed tissues, several potential mediators are to be found in the interstitial fluid and form an inflammatory exsudate ([ref. 50]), the content of which is acid and hyperosmotic ([ref. 51]). Consequently, the effect of hyperosmolarity on ASIC currents of cutaneous neurons of the spinal ganglia activated by moderate acidification was studied.

Figure 2:
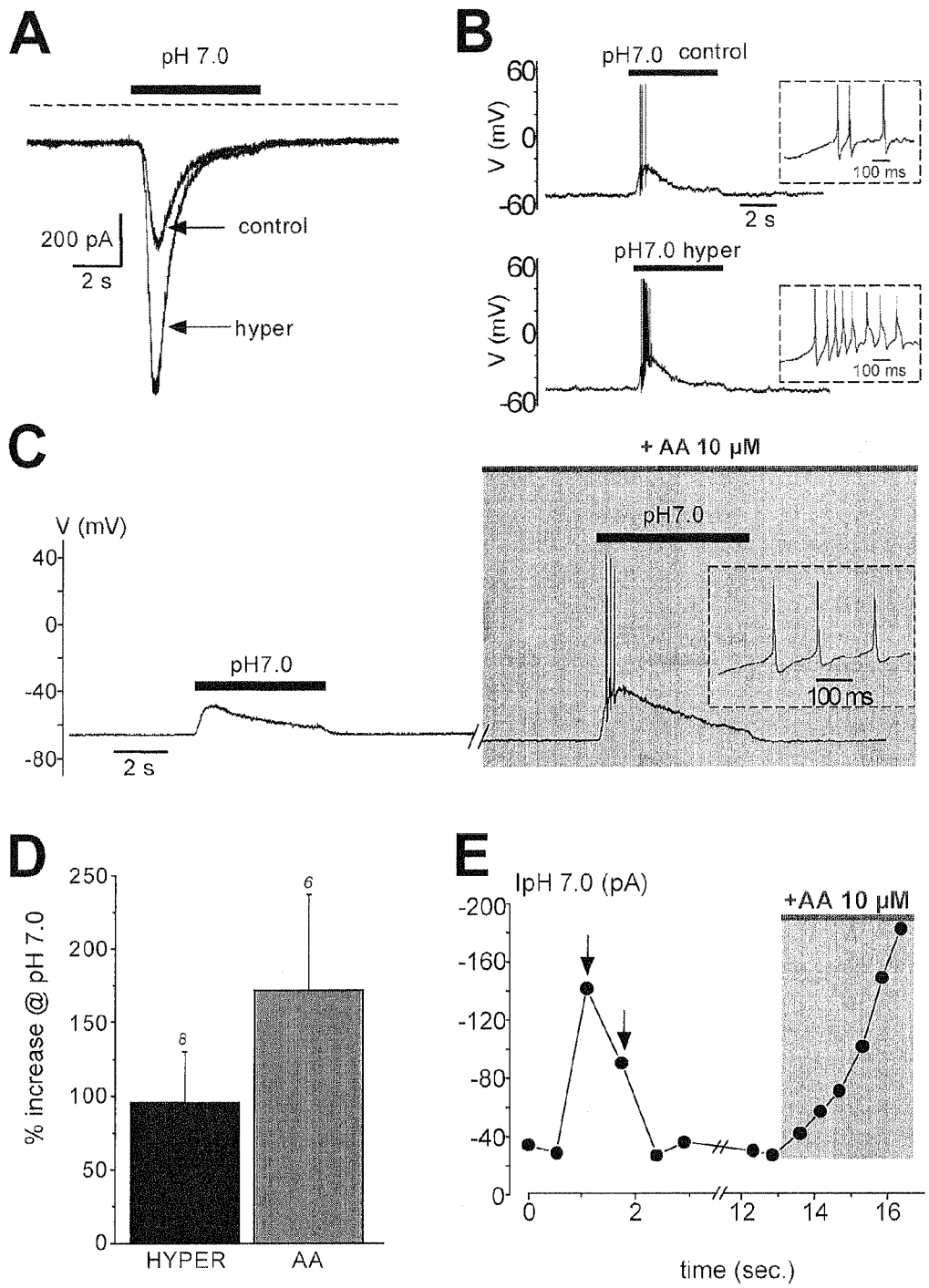
FIG. 2 shows the effect of osmotic pressure (hypertonicity) and of arachidonic acid on the native ASIC current induced by pH 7.0.

FIGS. 2A, 2D and 2E show that hyperosmolarity, concomitantly applied with external moderate acidification (pH 7.0, refer to arrows in FIG. 2E), is capable of markedly increasing the ASIC type current induced by pH 7.0 in these neurons (an increase of 95%±35%, n=8, P<0.01, Student's paired t test) resulting in an increase in neuronal excitability by inducing more action potentials (FIG. 2B).

A positive effect of the inflammatory mediator, arachidonic acid (AA), on the ASIC currents has already been described ([refs. 52 and 53]). This effect has been confirmed with the ASIC current induced by native pH 7.0 in cutaneous neurons of spinal ganglia (FIG. 2D; increase by 172±65%, n=6, P=0.06, Student's paired t test). Importantly, FIG. 2C shows that this effect of arachidonic acid also resulted in increased excitability of the cutaneous neurons of the spinal ganglia by increasing triggering of the action potential.

The kinetics of both effects differ. Indeed, FIG. 2E shows that whereas the potentiation induced by the native ASIC current's hyperosmolarity is immediate (concomitant application with the leap in pH), the effect of arachidonic acid on the ASIC current requires a few minutes in order to become fully operational. Furthermore, repeated applications of hyperosmolarity to the same cell lead to a reduction in the effect (refer to arrows), whereas the effect of arachidonic acid increases to a maximum for as long as it is applied to a cell (greyed box). Therefore, considered together, these results show that (i) the ASIC currents activated by moderate acidification (pH 7.0) in the cutaneous neurons of the spinal ganglia are of a sufficient level in order to bring the membrane potential to the triggering threshold of the action potentials, (ii) two inflammatory signals such as the hypertonicity of arachidonic acid enhance neuronal excitability through a potentiating effect on the ASIC current activated by moderate acidifications.

Example 4

Sensitivity of the Recombinant ASIC3 Channel to Osmotic Pressure in F-11 Cells Derived from Spinal Ganglia In order to analyze more precisely the effect of osmotic pressure on the different isoforms of ASIC, the ASIC1a and ASIC3 channels were expressed heterologously in the F-11 cell line ([refs. 44, 45, 46, 47], quoted above).

The ASIC1a and ASIC3 channels were used since (i) they are representative of the ASIC currents expressed in the neurons of the spinal ganglia of rats ([ref. 54] and [ref. 55], quoted above) (refer also to FIG. 1) and (ii) their liminal pH for activation is close to pH 7.0 ([ref. 2], quoted above).

Figure 3:
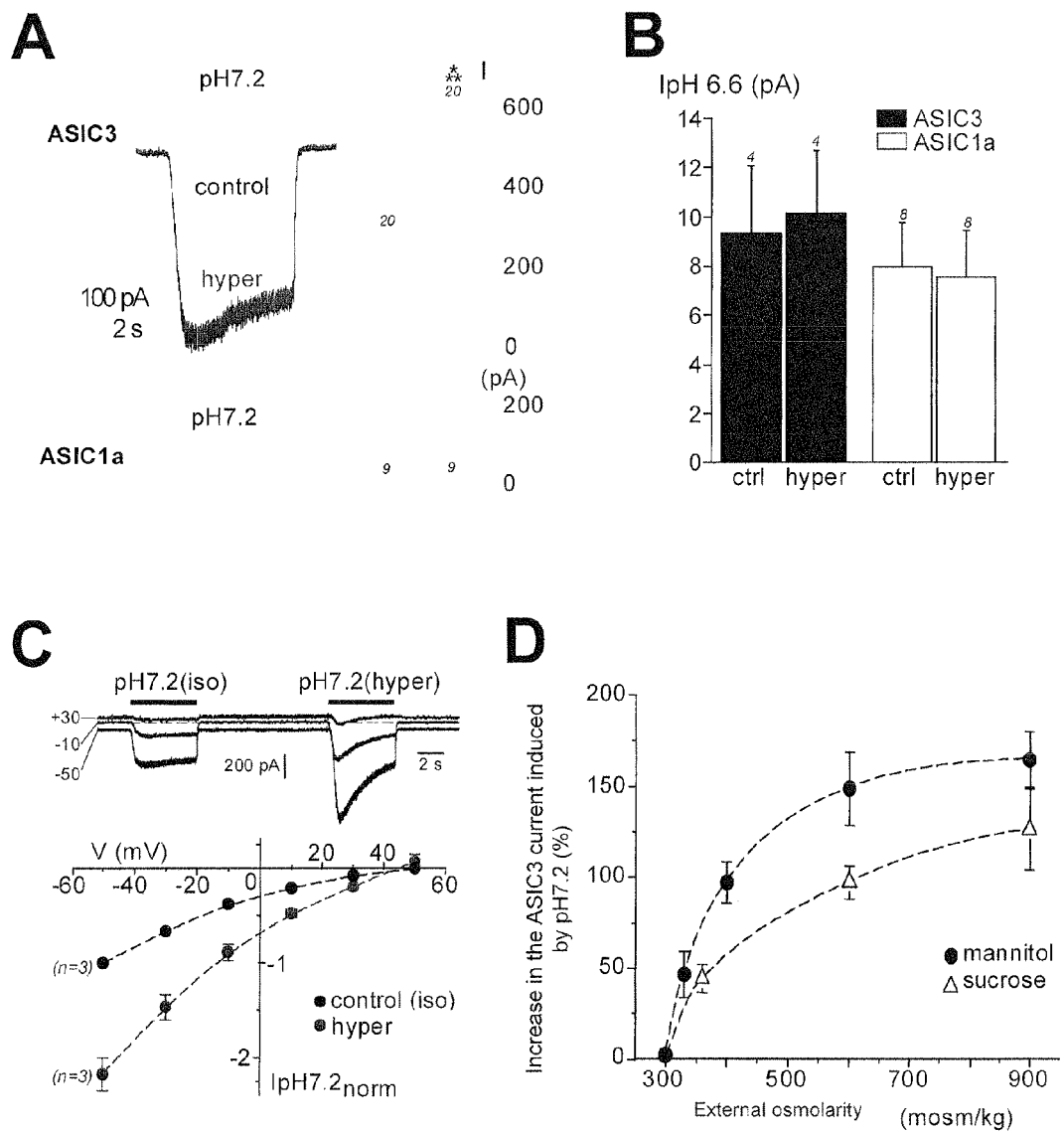
FIG. 3 shows the potentiation by hypertonicity of the recombinant ASIC1a and ASIC3 currents induced by moderate acidification.

FIG. 3A shows that hyperosmolarity (600 mosmol.kg$^{-1}$ with mannitol) is capable of significantly potentiating the ASIC3 current activated by pH 7.2 (an increase of 148±20%, n=20, P<0.001, Student's paired t test). On the other hand, external acidification to pH 7.2 does not produce any significant ASIC1a current from the cells transfected with ASIC1a and hyperosmolarity is devoid of effect. Interestingly, FIG. 3B shows that hyperosmolarity (600 mosmol.kg$^{-1}$), which is still devoid of effect on the ASIC1a current activated by pH 6.6, does not succeed in potentiating the ASIC3 current activated by pH 6.6, suggesting an effect on the non-inactivating, persistent ASIC3 window current ([ref. 19], quoted above).

In order to confirm that the ASIC3 current is potentiated by hyperosmotic shocks, the I/V curves of the current induced by pH 7.2 recorded from transfected F-11 cells were subsequently plotted (FIG. 3C, upper panel). The currents induced by pH 7.2 control (measurement under isotonic conditions) and increased (measurement under hypertonic conditions) have the same inversion potential (49.4±0.7 mV and 45.9±3.4 mV, respectively, P=0.48, Student's paired t test) (FIG. 3C, lower panel), indicating that hyperosmolarity actually potentiates the ASIC3 current.

FIG. 3D shows that the percentage increase in the ASIC3 current induced by pH 7.2 is almost at a maximum when the external osmolarity reaches 600 mosmol.kg$^{-1}$. Furthermore, hypertonicity is the primary factor in this effect to the extent that it is also observed, albeit with a slightly lesser amplitude, when the hyperosmotic external solutions have been prepared using sucrose (FIG. 3D).

These results indicate that hyperosmolarity potentiates the ASIC3 current within a moderate pH range (i.e. close to pH 7.2), probably through an effect on the ASIC3 window current.

Example 5

Potentiation of the Non-Inactivating ASIC3 Window Current by Arachidonic Acid

The effect of arachidonic acid (AA) was studied in F-11 cells transfected with ASIC1a and ASIC3 in order to examine the potentiating effect of arachidonic acid (AA) on ASIC type currents.

An effect of arachidonic acid on the activity of the ASIC channels has already been described ([ref. 52] and [ref. 53], quoted above), but the mechanism of the effect remains poorly understood.

Figure 4:
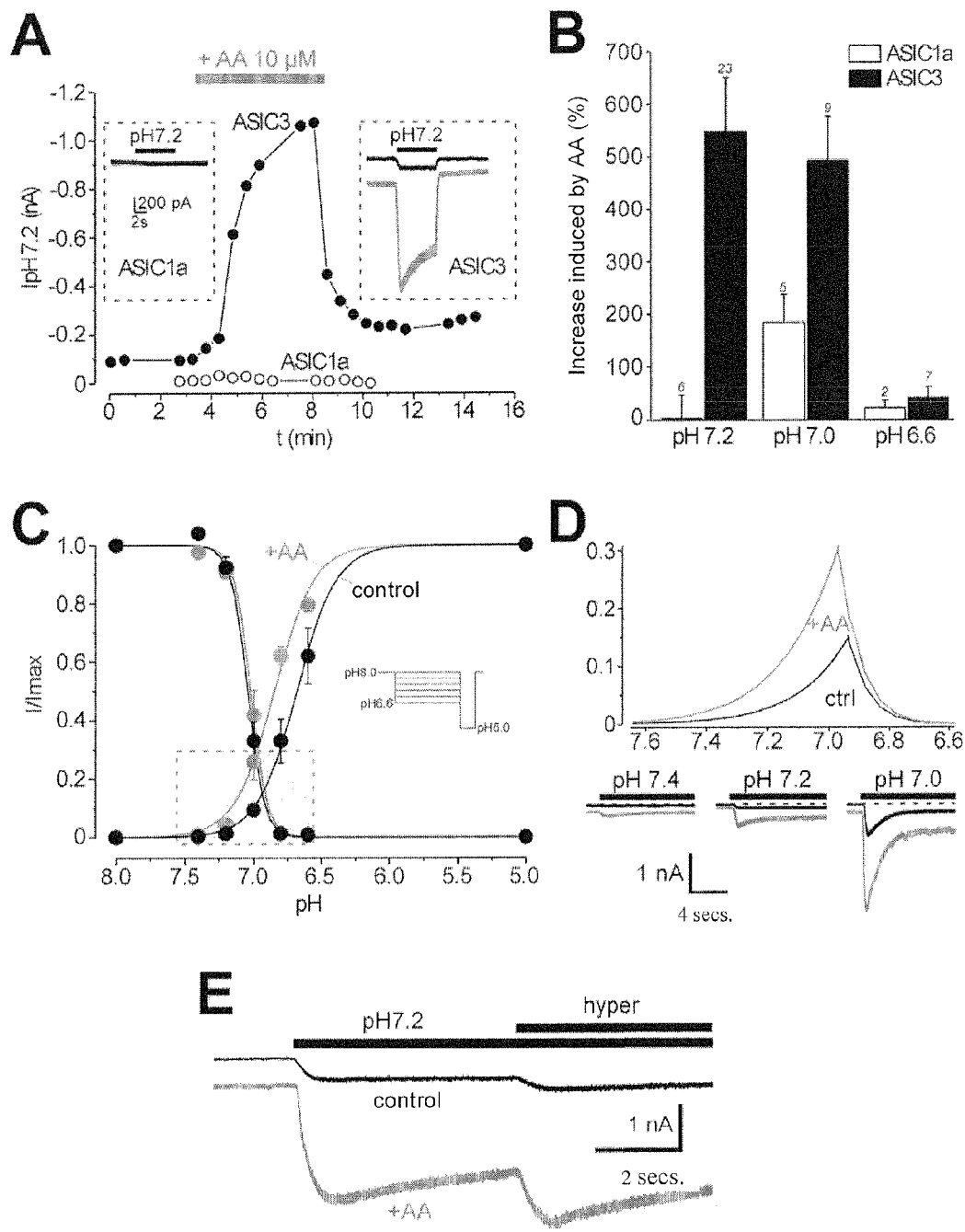
FIG. 4 shows the increase in the non-activating ASIC3 window current by the inflammatory mediator, arachidonic acid (AA), and the synergic effect on this arachidonic acid current and hypertonicity during moderate acidosis.

FIG. 4A shows that arachidonic acid results in a drastic reversible increase in the ASIC3 current activated by pH 7.2, whereas it does not have any effect on ASIC1a at the same pH. Arachidonic acid markedly potentiates the ASIC3 currents activated by pH 7.2 and pH 7.0 (an increase of 547±103%, P<0.0001, n=23 and 493±84%, P<0.0001, n=9, respectively, Wilcoxon test), whereas the ASIC3 current activated by pH 6.6 is only slightly increased (+40±22%, n=7, P=0.45, Student's paired t test) (refer to FIG. 4B). Consistently with the preceding results ([ref. 53], quoted above), arachidonic acid likewise increases the ASIC1a current at pH 7.0 (+183±54%, n=5, P=0.06, Wilcoxon test) and to a lesser degree at pH 6.6 (+21±15%, n=2), but this effect remains much less pronounced than for ASIC3 (FIG. 4E).

FIG. 4C shows that the powerful effect of arachidonic acid on the ASIC3 current is the result of a change in the dependence on pH of the activation towards more physiological values, whereas no significant effect is observed on the pH-dependent inactivation curve.

Consequently, the non-inactivating ASIC3 window current is markedly increased in the presence of arachidonic acid (FIG. 4D, upper panel), resulting in activation of the channel at pH values close to the resting physiological pH (i.e. pH 7.4) (FIG. 4D, lower panel).

These results indicate that arachidonic acid preferentially potentiates the ASIC3 currents activated by moderate acidity through a powerful effect on the non-inactivating window current. Highly significantly, FIG. 4E shows that this effect of arachidonic acid is an additive to the effect of hypertonicity on the same ASIC3 current. This result strongly suggests that ASIC3 may incorporate different inflammatory signals, such as moderate acidification, hypertonicity and arachidonic acid.

Example 6

Contribution of ASIC3 to Cutaneous Pain Induced by Moderate Acidification

The high expression of ASIC3 in the cutaneous neurons of the spinal ganglia and its modulation at moderate pH values by inflammatory stimuli, such as hyperosmolarity and arachidonic acid, led to investigate the role of ASIC3 in cutaneous acid pain under normal and inflammatory conditions.

Figure 5:
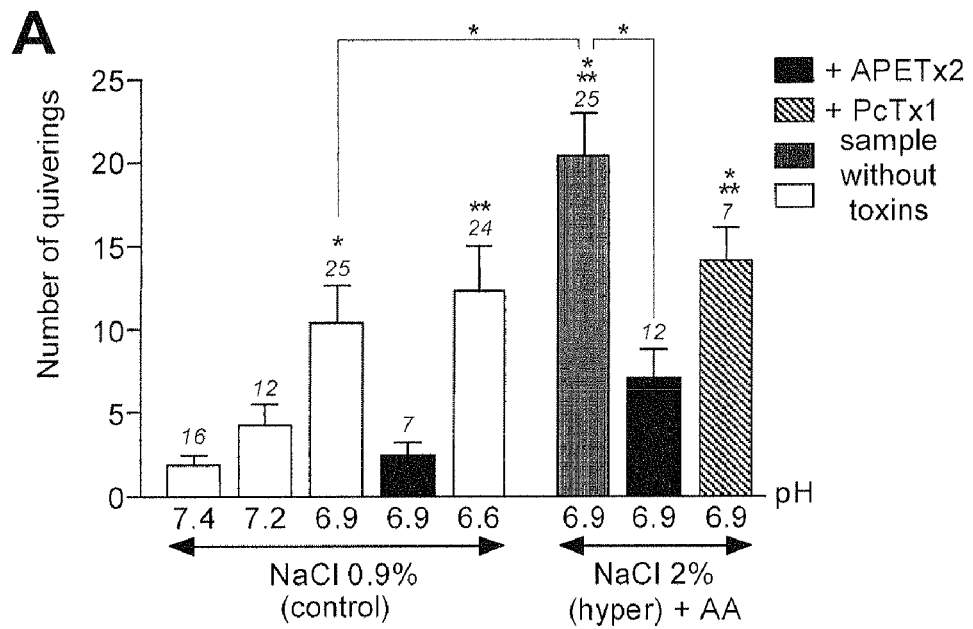
FIG. 5 represents the in vivo role of ASIC3 in acidic cutaneous pain, its positive modulation by inflammatory factors (arachidonic acid and hypertonicity) and its role in inflammatory thermal hyperalgesia.
Figure 5:
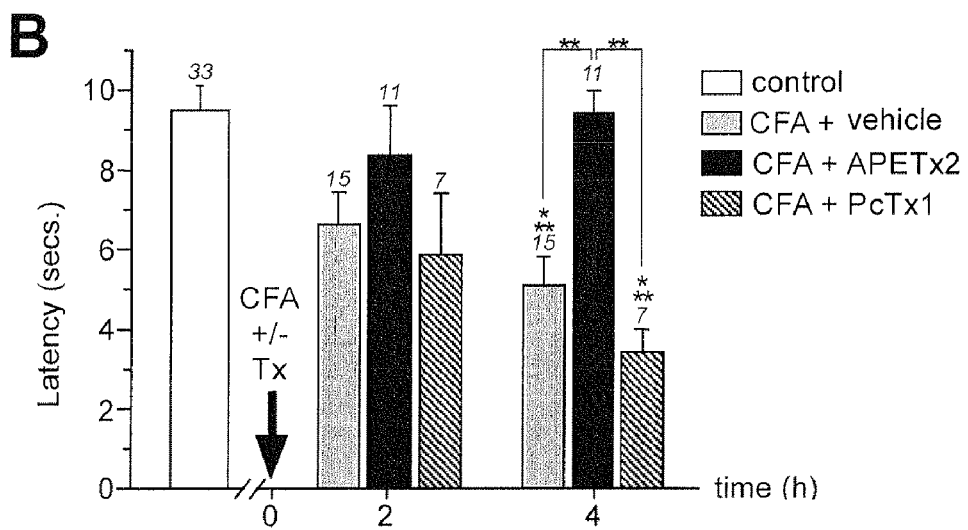

FIG. 5A shows the behaviour of rats in response to pain following subcutaneous injection of moderately acidic solutions (pH 7.4, pH 7.2, pH 6.9 and pH 6.6) into one of the hind paws. A significant behaviour in response to pain appears at pH 6.9 (the quivering score increases from $2.11\pm0.67$ at pH 7.4 to $11.11\pm2.54$ at pH 6.9, n=14 and 22, respectively, $P<0.05$, Kruskal-Wallis test followed post hoc by a Dunn's test). This pain behaviour is suppressed in the presence of APETx2 toxin, thereby demonstrating the involvement of ASIC3 in the detection of subcutaneous acid pain.

To the extent that hypertonicity and arachidonic acid appear to be strong synergic activators of the ASIC3 channel at a moderate pH both in the cutaneous neurons of the spinal ganglia and in F-11 cells expressing recombinant channels (refer to FIGS. 2, 3 and 4), these inflammatory signals were concomitantly injected (2% NaCl, ~600 mosmol.kg$^{-1}$ and 10 mM AA) at a moderate pH (FIG. 5A). The combination of these three essential elements of the inflammatory cocktail increases the quivering score of the rats in relation to the pH 6.9 alone (from $11.1\pm2.54$, n=22 to $20.42\pm2.53$, n=25, $P<0.05$, Kruskal-Wallis test, followed post hoc by a Dunn's test) (FIG. 5A).

This behaviour in response to acid pain was markedly reduced by the APETx2 peptide toxin, the specific inhibitor of ASIC3 ([ref. 38], quoted above), whereas the PcTx1 toxin, the specific inhibitor of ASIC1a, is devoid of any significant effect (FIG. 5A).

Considered together, these results strongly suggest that ASIC3 is the main receptor of cutaneous pain induced by moderate acidification and participates in inflammatory pain in rats.

Example 7

Contribution of ASIC3 to the Development of Thermal Hyperalgesia Induced by Inflammation Caused by Freund's Complete Adjuvant (CFA) in Rats The effects of the peptide toxins APETx2 (inhibitor of the channels containing the ASIC3 isoform) and PcTx1 (inhibitor of the ASIC1a homomer channels) were tested in a cutaneous pain model (thermal hyperalgesia induced by CFA) in rats in order to confirm the specific role of ASIC3 in inflammatory pain.

FIG. 5B shows that significant thermal hyperalgesia appears four hours after induction of inflammation by injection of CFA into a hind paw.

On the other hand, thermal hyperalgesia does not develop when the APETx2 peptide toxin is concomitantly injected with CFA, whereas the PcTx1 toxin is devoid of any significant effect.

Twenty hours after the injection of CFA, the animals treated with the APETx2 peptide toxin do not display any behaviour different from that of the control animals injected with the vehicle with respect to thermal hyperalgesia (data not represented), probably pointing to gradual waning of the effect of this toxin over time.

These results show that ASIC3, but not ASIC1a, plays a significant role in perception of inflammatory pain at a peripheral level in rats.

Example 8

Specific Inhibitory Effect of the APETx2 Toxin In Vivo

Demonstration of the specificity of ASIC3 channel inhibition by the APETx2 toxin at a cellular level (on cultured neurons and on transfected F-11 cell lines) led one to seek proof that the analgesic effects of APETx2 observed in rats were exclusively the result of inhibition of the ASIC3 type channel activity. An approach involving genetic inhibition of the ASIC3 channels was adopted for this purpose, and consisted in observing the effect of intrathecal injections of interfering RNA (iRNA) specifically directed at the ASIC3 channels in rats.

Figure 6:
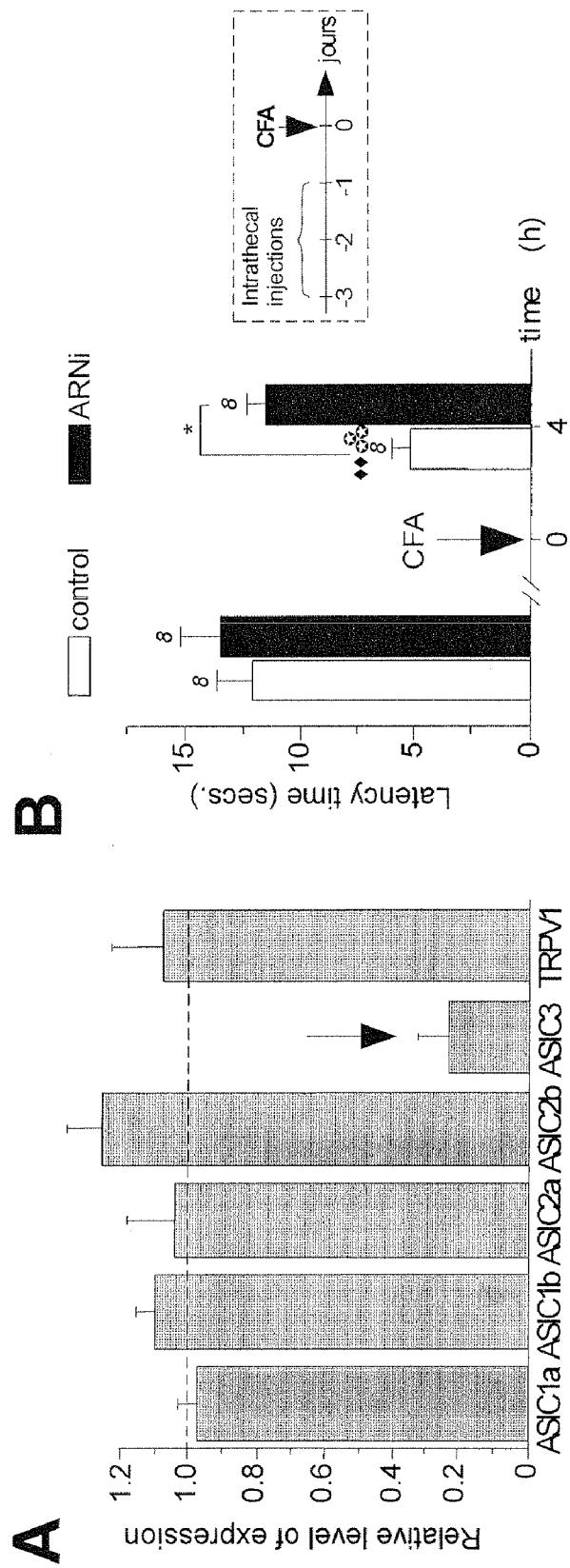
FIG. 6 represents the specific effect of intrathecal injection of interfering RNA (iRNA) directed against the ASIC3 messenger RNA on the levels of ASIC channel and TRPV1 channel messenger RNAs in the spinal ganglia and the analgesic effect of this iRNA in an model of inflammatory pain.

FIG. 6A shows the effect of intrathecal injections of iRNA specific to the ASIC3 channels on the expression levels of various ionic channels in rat sensory neurons that innervate the hind paws. The results show that the intrathecal injections of ASIC3 channel-specific iRNA allow a marked and exclusive reduction in the expression of the ASIC3 channels in the sensory neurons of rats (refer to black arrow).

FIG. 6B shows that rats intrathecally injected with ASIC3 channel-specific iRNA during the 3 days preceding induction of inflammation caused by Freund's complete adjuvant (CFA) (refer to insert) do not develop any inflammatory thermal hyperalgesia (iRNA, black column) versus control rats treated with iRNA of identical composition but with a random sequence (control, white column). This result is identical to that obtained with the animals treated with the APETx2 toxin (refer to example 7).

These results prove that the ASIC3 channels are mediators of inflammatory pain and that the analgesic effects of the APETx2 toxin result exclusively from the blocking of these channels in the animal.

Example 9

Inhibitory Effect of the APETx2 Toxin on the Human ASIC3 Clone

The inhibitory effect of the APETx2 peptide toxin was studied on human ASIC3 channels. To this end, the amplitude of the human ASIC3 currents was recorded according to the patch clamp method described above, following acidifications of the extracellular medium (pH 8.0 to pH 7.0, refer to double arrow), in the absence or presence of the APETx2 toxin at 1 μM, from F-11 sensory neurons transfected with the human ASIC3 clone according to the method described above.

Figure 7:
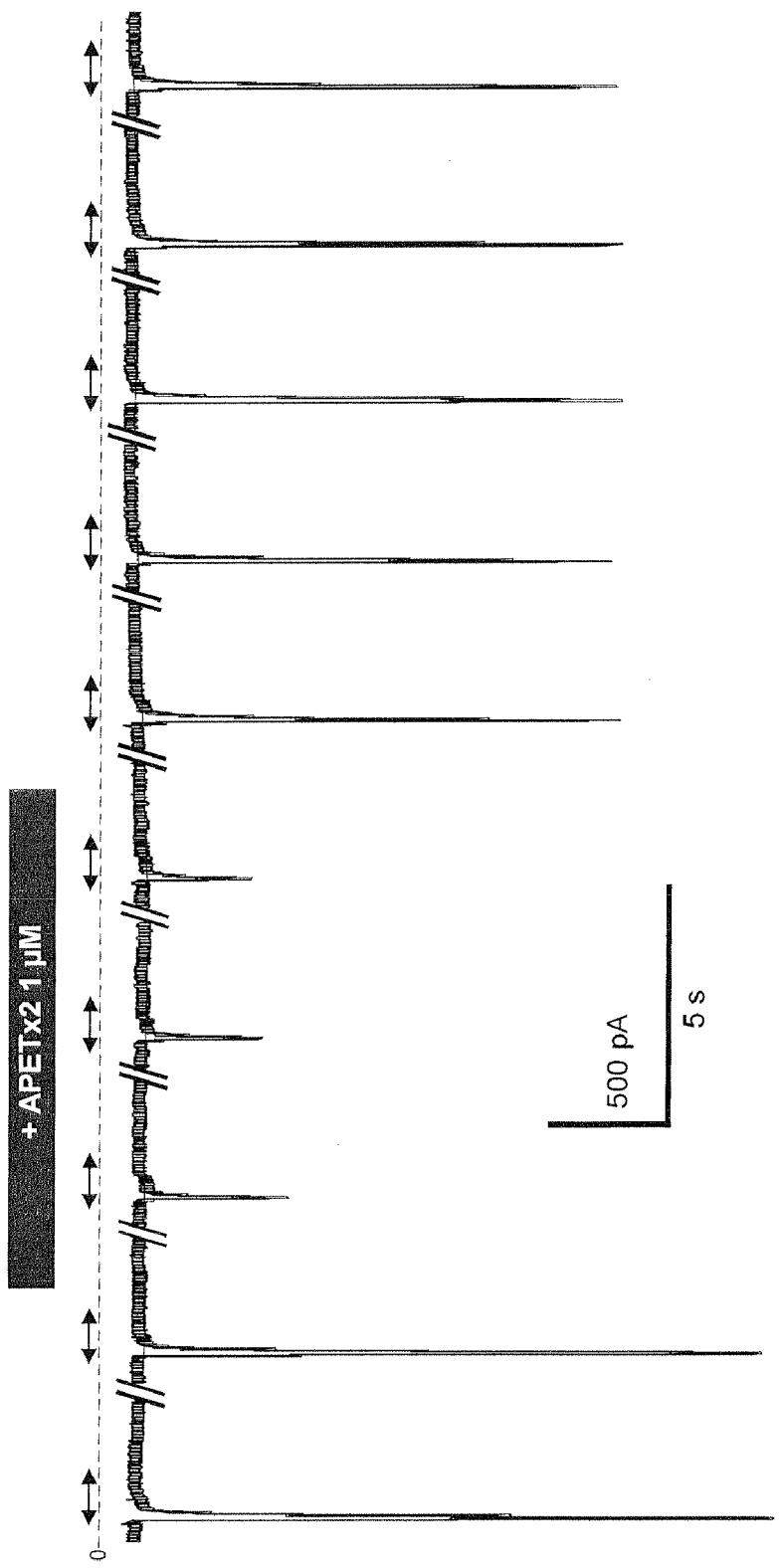
FIG. 7 represents the effect of the APETx2 toxin on the activity of the human ASIC3 channels expressed in the sensory neuron line F11.

FIG. 7 shows that the amplitude of the currents derived from the human ASIC3 channels is significantly reduced in the presence of the APETx2 toxin ($3^{rd}$ and $5^{th}$ peaks starting from the left).

These results clearly indicate that the APETx2 toxin is capable of inhibiting the activity of the human ASIC3 channels and validate potential use of the APETx2 toxin and its derivatives as a new painkiller in humans.

LISTS OF REFERENCES

[ref. 1] Wemmie and aL, Trends Neurosci., 29: 578-586, 2006
[ref. 2] Lingueglia, J. Biol. Chem., 282: 17325-17329, 2007
[ref. 3] Jasti and aL, Nature, 449: 316-323, 2007
[ref. 4] Lingueglia and aL, J. Biol. Chem., 272: 29778-29783, 1997
[ref. 5] Benson and aL, Proc. Natl. Acad. Sci. U.S.A., 95: 10240-10245, 2002
[ref. 6] Hesselager and al., J. Biol. Chem., 279: 11006-11015, 2004
[ref. 7] Waldmann and sI., J. Biol. Chem., 272: 20975-20978, 1997a
[ref. 8] Bassler and al., J. Biol. Chem., 276: 33782-33787, 2001
[ref. 9] Reeh & Steen, Prog. Brain Res., 113: 143-151, 1996
[ref. 10] Woo and aL, Anesthesiology, 101: 468-475, 2004
[ref. 11] Steen and aL, Neurosci. Lett., 199: 29-32, 1995a
[ref. 12] Issberner and aL, Neurosci. Lett., 208: 191-194, 1996
[ref. 13] Ogawa and al., J. Clin. Invest., 110: 1185-1190, 2002
[ref. 14] Jones and aL, J. Neurosci., 24: 10974-10979, 2004
[ref. 15] Waldmann and aL, Nature, 386: 173-177, 1997b
[ref. 16] Dube and aL, Pain, 117: 88-96, 2005
[ref. 17] Voilley and aL, J. Neurosci., 21: 8026-8033, 2001
[ref. 18] Molliver and aL, Mol. Pain, 1: 35, 2005
[ref. 19] Vagi and aL, Circ. Res., 99: 501-509, 2006
[ref. 20] Sutherland and aL, Proc. Nat. Acad. Sci. USA, 98: 711-716, 2001
[ref. 21] Priee and aL, Neuron, 32: 1071-1083, 2001
[ref. 22] Sluka and aL, Pain, 106: 229-239, 2003
[ref. 23] Sluka and aL, Pain, 129: 102-112, 2007
[ref. 24] Xie and aL, J. Neurophysiol., 87: 2835-2843, 2002
[ref. 25] Chen and aL, Proc. Natl. Aead. Sci. U.S.A., 99: 8992-8997, 2002
[ref. 26] Babinski and aL, J. Biol. Chem., 275: 28519-28525, 2000
[ref. 27] Askwith and aL, Neuron, 26: 133-141, 2000
[ref. 28] Moezydlowski and al., J. Membr. Biol., 105: 95-111, 1988
[ref. 29] Norton, Toxicon, 29: 1051-1084, 1991
[ref. 30] Harvey and aL, Ann. NY Acad. Sci., 710:1-10, 1994
[ref. 31] Uehitel, Toxicon, 35: 1161-1191, 1997
[ref. 32] Tytgat and aL, Trends Pharmacol. Sci., 20: 444-447, 1999
[ref. 33] Eseoubas and al., Biochimie, 82: 893-907, 2000b
[ref. 34] Hugues and aL, Proc. Nat. Acad. Sei. USA, 79: 1308-1312, 1982
[ref. 35] Shakkottai and aL, J. Biol. Chem., 276: 43145-43151, 2001
[ref. 36] Eseoubas and aL, J. Biol. Chem., 275(33): 25116-25121, 2000
[ref. 37] Mazzuea and al., Nature Neurosci., 10(8): 943-945, 2007
[ref. 38] Dioehot and aL, Embo J., 23: 1516-1525, 2004
[ref. 39] Bruhn and al., Toxicon, 39: 693-702, 2001
[ref. 40] Dioehot and aL, Mol. Pharmacol., 64: 59-69, 2003
[ref. 41] Dioehot and aL, J. Biol. Chem., 273: 6744-6749, 1998
[ref. 42] Wu and aL, Anal. Biochem., 235: 161-174, 1996
[ref. 43] Chagot and aL, Protein Sci., 14: 2003-2010, 2005
[ref. 44] Platika and aL, Proc. Natl. Aead. Sci. U.S.A., 82: 3499-3503, 1985
[ref. 45] Franeel and aL, J. Neuroehem., 48: 1624-1631, 1987
[ref. 46] Deval and aL, J. Biol. Chem., 281: 1796-1807, 2006
[ref. 47] Ettaiche and aL., J. Neurosei., 26: 5800-5809, 2006
[ref. 48] Hamill and aL, Pflugers Arch., 391: 85-100, 1981
[ref. 49] Tominaga and aL, Neuron, 21: 531-543, 1998
[ref. 50] Steen and aL, J. Neurosci., 15: 3982-3989, 1995b
[ref. 51] Vakili and aL, Surg. Forum, 21: 227-228, 1970
[ref. 52] Allen & Attwell, J. Physiol., 543: 521-529, 2002
[ref. 53] Smith and al., Neuroscience, 145: 686-698, 2007
[ref. 54] Mamet and al., J. Neurosci., 22: 10662-10670, 2002
[ref. 55] Oeval and al., Neuropharmacology, 44: 662-671, 2003
[ref. 56] Qi and al., Biochemistry, 40: 4531-4538, 2001
[ref. 57] Chen and al., Proc. Natl. Aead. Sci. U.S.A., 95: 10240-10245, 1998
[ref. 58] Bode and al., Nature, 409: 35-36, 2001
[ref. 59] Alessandri-Haber and aL, Pain, 118: 70-79, 2005
[ref. 60] Ikeuehi and aL, J. Pain, 1 0: 336-342, 2009
[ref. 61] Stander and Sehmelz, Eur. J. Pain, 10: 473-478

The invention claimed is:

1. A method of treating pain or itching in a subject in need thereof the method comprising administering to the subject a pharmaceutical composition comprising a therapeutically effective amount of the APETx2 peptide toxin of the *Anthopleura elegantissima* sea anemone and a pharmaceutically acceptable excipient.

2. The method of claim 1 wherein said administering is via a peripheral route.

3. The method of claim 1 wherein said administering is via the subcutaneous route.

4. The method of claim 1 wherein said administering is via the intramuscular route.

5. The method of claim 1 wherein said administering is via the transdermal or cutaneous route.

6. The method of claim 1 wherein said administering is via the systemic route.

7. A method of treating pain or itching in a subject in need thereof, the method comprising administering to the subject a therapeutically effective amount of the APETx2 peptide toxin of the *Anthopleura elegantissima* sea anemone comprising GTACSCGNSKGIYWFYRPSCPTDRGYTG-SCRYFLGTCCTPAD (SEQ ID NO:3) or a biologically active fragment or variant thereof, wherein said variant is a peptide comprising SEQ NO: 3 in which a non-native amino acid residue has been substituted for the native amino acid residue at one or more of positions 3, 5, 8, 9,10, 15, 16, 17, 23, 31, 32, 33, 36, 39 or 41, and wherein said biological activity is the inhibition of ASIC3 channel.

8. The method according to claim 7 wherein the effective amount is effective for treating pain or itching associated with a condition selected from the group consisting of ischaemias, fractures, haematomas, oedemas, phlyctenae, local infections, tissue lesions, eye injuries, inflammation, tissue acidosis and tumours.

9. The method of claim 1 or 7, wherein said treating of itching delays or inhibits itching.

10. A method of inhibiting the ASIC3 type channel in a subject with pain or itching the method comprising administering to the subject an ASIC3 type channel inhibiting amount of the APETx2 peptide comprising GTACSCGNSKGIYWFYRPSCPTDRGYTG-SRYFLGTCCTPAD(SEQ ID NO: 3) or a biologically active fragment or variant thereof, wherein said variant is a peptide comprising SEQ ID NO: 3 in which a non-active amino acid residue has been substituted for the native amino acid residue at one or more positions 3, 5, 8, 9, 10, 15, 16, 17, 23, 31, 32, 33, 36, 39 or 41, and wherein said biological activity is the inhibition of ASIC3 channel.

* * * * *

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: iRNA specific of the ASIC3 channels

<400> SEQUENCE: 1
ctacacgcta tgccaagga                                                  19
```

```
<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: iRNA control

<400> SEQUENCE: 2
gctcacacta cgcagagat                                                        19

<210> SEQ ID NO 3
<211> LENGTH: 42
<212> TYPE: PRT
<213> ORGANISM: Anthopleura elegantissima

<400> SEQUENCE: 3

Gly Thr Ala Cys Ser Cys Gly Asn Ser Lys Gly Ile Tyr Trp Phe Tyr
1               5                   10                  15

Arg Pro Ser Cys Pro Thr Asp Arg Gly Tyr Thr Gly Ser Cys Arg Tyr
            20                  25                  30

Phe Leu Gly Thr Cys Cys Thr Pro Ala Asp
            35                  40
```